United States Patent
Coleman et al.

(10) Patent No.: US 7,625,392 B2
(45) Date of Patent: Dec. 1, 2009

(54) WOUND CLOSURE DEVICES AND METHODS

(76) Inventors: James Coleman, 20 Greenmount Road, Terenure, Dublin 6 (IE); Christy Cummins, 9 Furness Manor, Johnstown, Nars, County Kildare (IE)

( * ) Notice: Subject to any disclaimer, the term of this patent is extended or adjusted under 35 U.S.C. 154(b) by 547 days.

(21) Appl. No.: 11/307,372

(22) Filed: Feb. 3, 2006

(65) Prior Publication Data
US 2007/0185529 A1    Aug. 9, 2007

(51) Int. Cl.
*A61B 17/08* (2006.01)
(52) U.S. Cl. ................. 606/213; 606/151; 606/158
(58) Field of Classification Search ........... 606/213, 606/215, 216; 411/34, 38, 62, 33
See application file for complete search history.

(56) References Cited

U.S. PATENT DOCUMENTS

| | | | |
|---|---|---|---|
| 3,942,407 A * | 3/1976 | Mortensen | ............ 411/36 |
| 5,035,702 A | 7/1991 | Taheri | |
| 5,197,971 A | 3/1993 | Bonutti | |
| 5,741,297 A | 4/1998 | Simon | |
| 6,183,496 B1 * | 2/2001 | Urbanski | ............ 606/213 |
| 6,261,309 B1 | 7/2001 | Urbanski | |
| 6,312,446 B1 | 11/2001 | Huebsch et al. | |
| 6,355,052 B1 | 3/2002 | Neuss et al. | |
| 6,375,671 B1 | 4/2002 | Kobayashi et al. | |
| 6,616,685 B2 | 9/2003 | Rousseau | |
| 6,623,508 B2 | 9/2003 | Shaw et al. | |
| 6,776,785 B1 | 8/2004 | Yencho et al. | |
| 6,960,224 B2 | 11/2005 | Marino et al. | |
| 7,018,388 B2 | 3/2006 | Yencho et al. | |
| 7,022,127 B2 | 4/2006 | Suyker et al. | |
| 7,108,702 B2 | 9/2006 | Yencho et al. | |
| 7,149,587 B2 * | 12/2006 | Wardle et al. | ............ 607/126 |
| 2003/0171774 A1 | 9/2003 | Freudenthal et al. | |

(Continued)

FOREIGN PATENT DOCUMENTS

EP    1908419 A1    4/2008

(Continued)

OTHER PUBLICATIONS

Examination Communication from EPO dated Apr. 30, 2009 (European Patent Application No. 077032411.5).

(Continued)

*Primary Examiner*—(Jackie) Tan-Uyen T. Ho
*Assistant Examiner*—Alexander Orkin
(74) *Attorney, Agent, or Firm*—Nutter McClennen & Fish LLP

(57) ABSTRACT

Methods and devices are provided for closing a puncture wound. In one exemplary embodiment, a puncture closure device is provided having an elongate tubular body that is disposable through a puncture in tissue and that includes proximal and distal portions. The proximal portion can be adapted to expand to form proximal wings upon rotation of the elongate tubular body, preferably in a first direction. The distal portion can be adapted to expand to form distal wings upon rotation of the elongate tubular body, preferably in a second, opposite direction. The proximal and distal portions can also be adapted to be moved toward one another as they expand upon rotation. As a result, the proximal and distal wings can engage tissue therebetween.

40 Claims, 14 Drawing Sheets

U.S. PATENT DOCUMENTS

| | | |
|---|---|---|
| 2004/0243155 A1* | 12/2004 | Yencho et al. ............... 606/153 |
| 2005/0043759 A1 | 2/2005 | Chanduszko |
| 2005/0055050 A1 | 3/2005 | Alfaro |
| 2005/0075665 A1* | 4/2005 | Brenzel et al. .............. 606/213 |
| 2005/0149071 A1 | 7/2005 | Abbott et al. |
| 2005/0267524 A1 | 12/2005 | Chanduszko |
| 2005/0273124 A1 | 12/2005 | Chanduszko |
| 2006/0196137 A1* | 9/2006 | Brenzel et al. ........... 52/506.02 |
| 2006/0217748 A1 | 9/2006 | Ortiz |
| 2006/0265004 A1* | 11/2006 | Callaghan et al. ........... 606/213 |
| 2007/0021758 A1 | 1/2007 | Ortiz |
| 2007/0185529 A1 | 8/2007 | Coleman et al. |
| 2009/0105733 A1 | 4/2009 | Coleman et al. |

FOREIGN PATENT DOCUMENTS

| | | |
|---|---|---|
| WO | 0009040 A1 | 2/2000 |
| WO | 0149185 | 7/2001 |
| WO | 0205718 A2 | 1/2002 |
| WO | 2007013070 A1 | 2/2007 |
| WO | 2007073566 A1 | 6/2007 |
| WO | 2008040577 A1 | 4/2008 |

OTHER PUBLICATIONS

International Application No. PCTEP2008008178 Search Report dated Jun. 8, 2009, 23 pgs.

* cited by examiner

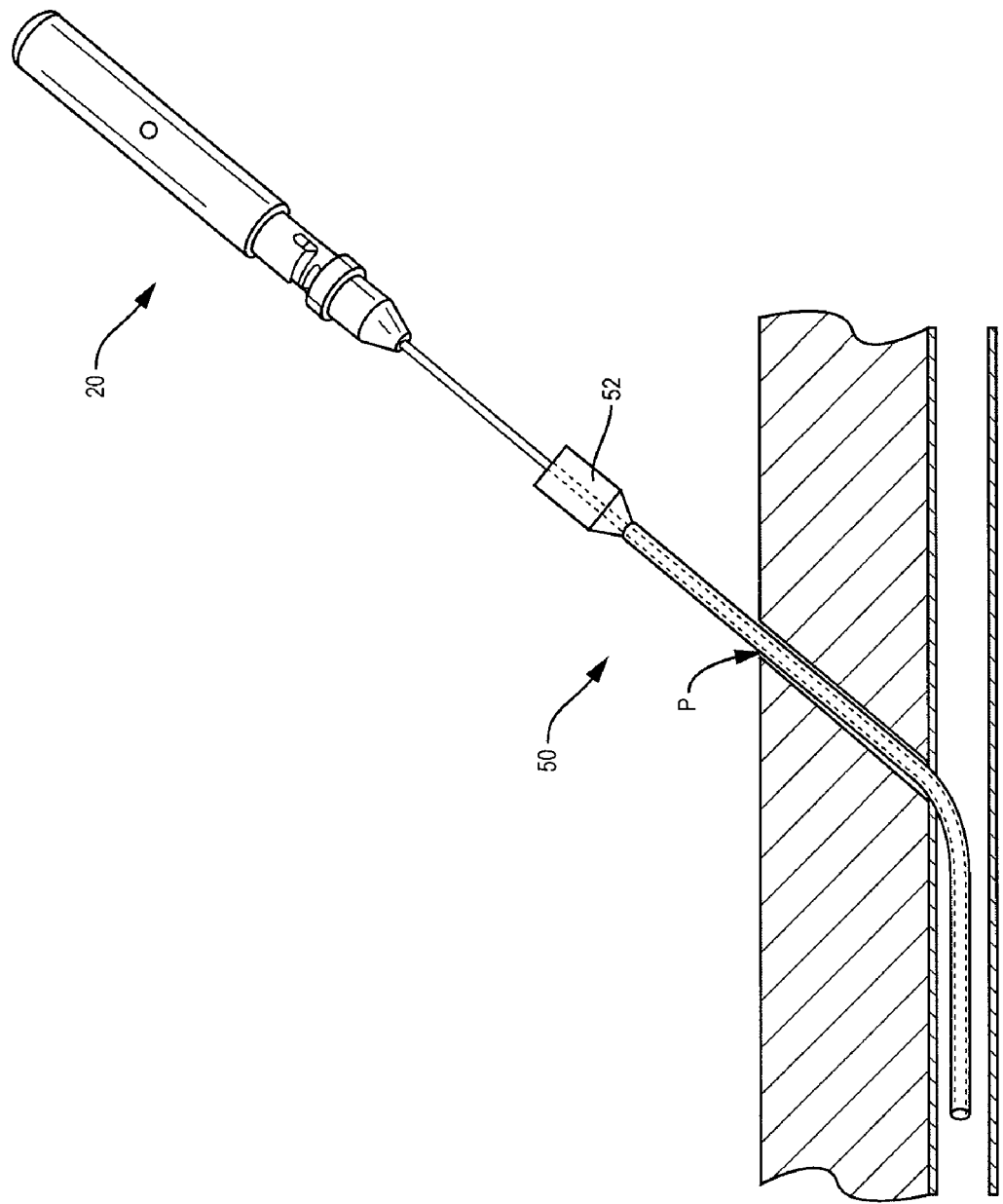

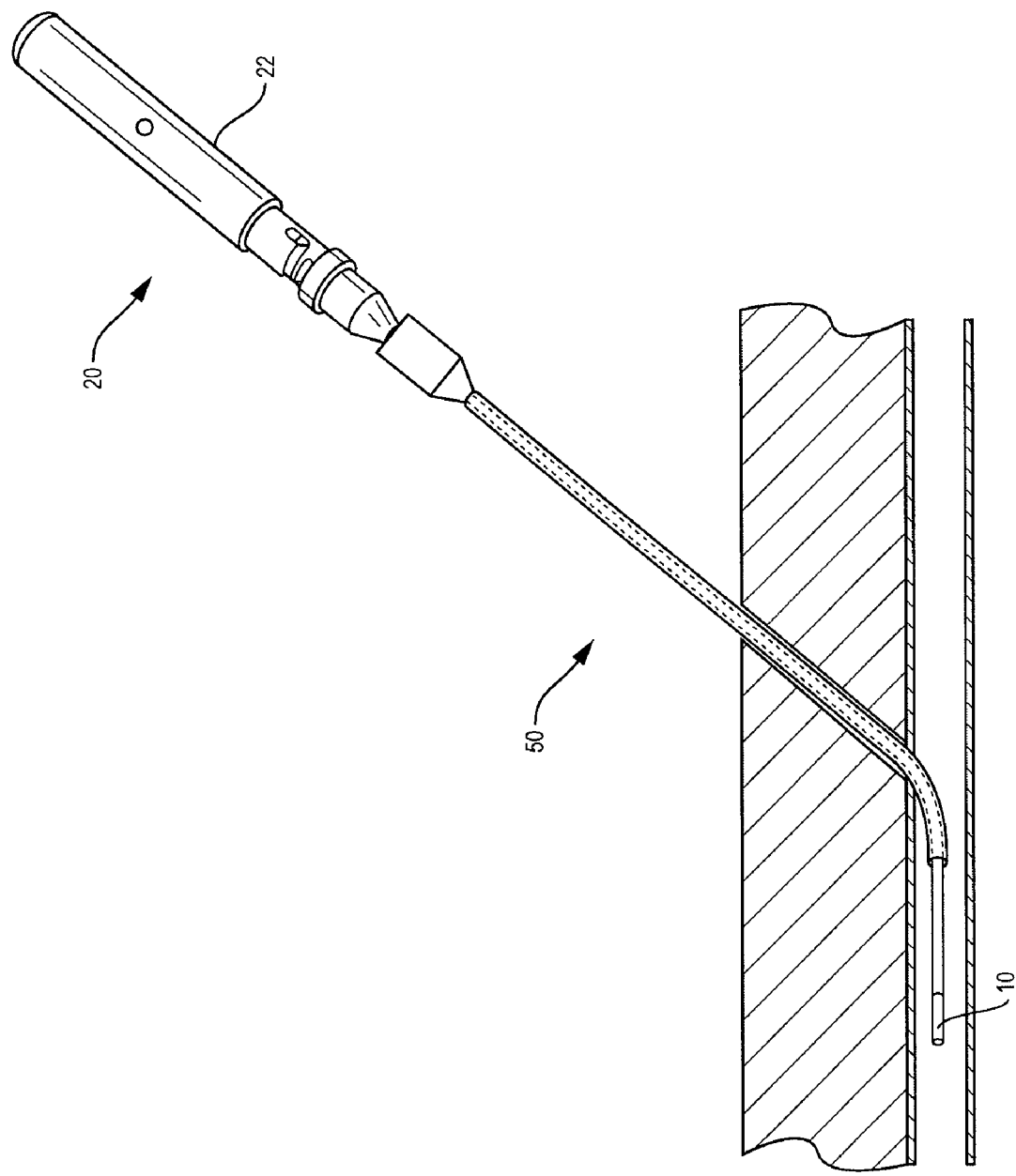

WOUND CLOSURE DEVICES AND METHODS

FIELD OF THE INVENTION

The present invention relates to methods and devices for closing a vascular puncture wound.

BACKGROUND OF THE INVENTION

Catheterization and interventional procedures, such as angioplasty or stenting, generally are performed by inserting a hollow needle through a patient's skin and intervening tissue into the vascular system. A guidewire may then be passed through the needle lumen into the patient's blood vessel accessed by the needle. The needle may be removed, and the introducer sheath may be advanced over the guidewire into the vessel e.g. in conjunction with or subsequent to a dilator. A catheter or other device may then be advanced through a lumen of the introducer sheath and over the guidewire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath may be removed, leaving a puncture site in the vessel wall. External pressure may be applied to the puncture site until clotting and wound sealing occur. This procedure however, may be time consuming and expensive requiring as much as an hour of a physician or assistant's time. It is also uncomfortable for the patient and requires that the patient remain immobilized in the operating room, catheter lab, or holding area. In addition a risk of a hematoma exists from bleeding before hemostasis occurs.

Various apparatus have been suggested for percutaneously sealing a vascular puncture by occluding the puncture site. One apparatus is a biodegradable plug that is delivered through an introducer sheath into a puncture site. When deployed, the plug seals the vessel and provides hemostasis. Such plugs, however, may be difficult to position properly with respect to the vessel. Moreover, it is generally undesirable to expose the plugged material, e.g. collagen, to the blood stream where it may float down stream and risk causing an embolism. Another technique involves percutaneously suturing the puncture site. Percutaneous suturing devices, however, may require significant skills by the user and may be mechanical complex and expensive to manufacture.

Other closure devices include surgical fasteners. One known surgical fastener includes an annular base having legs that, in a relaxed state, extend in a direction substantially perpendicular to a plane defined by the base and slightly inwards toward one another. During use, the fastener is fit around the outside of a cannula, thereby deflecting the legs outward. The cannula is placed in an incision, and the fastener is slid along the cannula until the legs pierce into the blood vessel. When the cannula is withdrawn, the legs move towards one another and back to the relaxed state to close the incision. Staples can also be used to close a wound or incision. Staples, however, tend to have a large cross-sectional profile and therefore may not be easy to deliver through a percutaneous site to close an opening in a vessel wall.

Accordingly, improved methods and devices for closing a vascular puncture wound are needed.

BRIEF SUMMARY OF THE INVENTION

The present invention generally provides methods and devices for closing a puncture wound. In one exemplary embodiment, a puncture closure device is provided having an elongate tubular body that is disposable through a puncture in tissue and that includes proximal and distal portions. The proximal portion can be adapted to expand to form proximal wings upon rotation of part of the elongate tubular body, preferably in a first direction. The distal portion can be adapted to expand to form distal wings upon rotation of part of the elongate tubular body, preferably in a second, opposite direction. The proximal and distal portions can also be adapted to be moved toward one another as they expand upon rotation. As a result, the proximal and distal wings can engage tissue therebetween.

While the proximal and distal portions can have a variety of configurations, in one exemplary embodiment the proximal and distal portions can each include a plurality of slits formed therein and configured to allow portions of the elongate tubular body surrounding the plurality of slits to expand to form the proximal and distal wings. In an exemplary embodiment, the slits in the proximal portion extend in a first direction around a circumference of the elongate tubular body, and the slits in the distal portion extend in a second opposite direction around the circumference of the elongate tubular body. In another embodiment, the proximal wings can extend in a plane that is substantially parallel to a plane in which the distal wings extend. The proximal and distal wings can also be spaced a distance apart from one another to allow tissue to be engaged therebetween.

The device can also include an elongate shaft extending through and attached to a distal end of the elongate tubular body. In an exemplary embodiment, the elongate shaft can include a frangible portion configured to allow at least a proximal portion of the elongate shaft to be broken away from a distal portion of the elongate shaft or from the elongate tubular body. The device can also include an actuator coupled to the elongate tubular body and adapted to rotate at least a portion of the elongate tubular body. In certain exemplary embodiments, the actuator can be removably coupled to a proximal end of the elongate tubular body. In another exemplary embodiment, the elongate tubular body can be formed from a deformable material and/or a resorbable material.

A system for closing a puncture in tissue is also provided and includes an elongate tubular body having proximal and distal portions with a plurality of slits formed therein. The elongate tubular body can be adapted to extend outwardly between each of the plurality of slits formed in the proximal and distal portions such that the proximal and distal portions are adapted to engage tissue therebetween. The elongate tubular body can also include a mid-portion formed between the proximal and distal portions and adapted to be positioned within a puncture hole formed in tissue engaged between the proximal and distal portions. In one exemplary embodiment, the slits in the proximal portion can extend in a first direction around a circumference of the elongate tubular body, and the slits in the distal portion can extend in a second opposite direction around the circumference of the elongate tubular body. The proximal portion can thus be adapted to extend outwardly when rotated in a first direction, and the distal portion can be adapted to extend outwardly when rotated in a second opposite direction. The elongate tubular body can also include an elongate shaft extending therethrough and attached to a distal end thereof. The elongate shaft can include a frangible portion configured to allow at least a proximal portion of the elongate shaft to be broken away from a distal portion of the elongate shaft.

The system can further include an actuator removably coupled to the elongate tubular body and adapted to apply an axial and rotational force to the elongate tubular body to cause the elongate tubular body to extend outwardly. In one exemplary embodiment, the actuator includes an outer shaft that is removably coupled to a proximal end of the elongate tubular body. The outer shaft can include, for example, a protrusion formed therein and adapted to extend into a corresponding groove formed on the proximal end of the elongate tubular body for removably coupling the outer shaft to the elongate tubular body. The actuator can also include an elongate shaft that extends through and couples to a distal end of the elongate tubular body. The outer shaft can be rotatably disposed around the elongate shaft to allow the outer shaft to apply axial and rotational forces to the elongate tubular body.

A method for closing a puncture in tissue is also provided and in one exemplary embodiment the method can include inserting an elongate tubular body through a puncture in tissue, for example by inserting the body through an introducer sheath that guides the elongate tubular body through tissue. The sheath can optionally be predisposed within the puncture. The proximal and distal portions of the elongate tubular body can then be rotated to expand the proximal and distal portions such that tissue surrounding the puncture is engaged between the expanded proximal and distal portions thereby sealing the puncture. In an exemplary embodiment, prior to rotating the body, the proximal and distal portions of the elongate tubular body are positioned through the puncture on a first side of the tissue. The body can be rotated by, for example, rotating and expanding the distal portion, retracting the elongate tubular body until the expanded distal portion engages tissue, and rotating and expanding the proximal portion. The distal portion is preferably rotated and expanded before rotating and expanding the proximal portion of the elongate tubular body. The proximal and distal portions can also optionally be compressed as they are expanded and rotated. For example, the proximal and distal portions can be advanced in a distal direction while rotating the proximal and distal portions. In an exemplary embodiment, proximal and distal portions are rotated using an actuator. The actuator can include an outer shaft that is rotated in a first direction to rotate and expand the distal portion of the elongate tubular body, and that is rotated in a second opposite direction to rotate and expand the proximal portion of the elongate tubular body. Preferably, the outer shaft is rotated relative to an elongate shaft that is coupled to a distal end of the elongate tubular body. The elongate shaft can optionally be broken away from the elongate tubular body once the body is implanted. This can be achieved, for example, by rotating the elongate shaft. In other embodiments, inserting the elongate tubular body can include guiding the elongate tubular body along a guidewire predisposed within a lumen containing the puncture, and/or viewing blood flashback from a lumen containing the puncture to confirm that the elongate tubular body has passed through the puncture.

BRIEF DESCRIPTION OF THE DRAWINGS

The invention will be more fully understood from the following detailed description taken in conjunction with the accompanying drawings, in which.

Figure 1A:
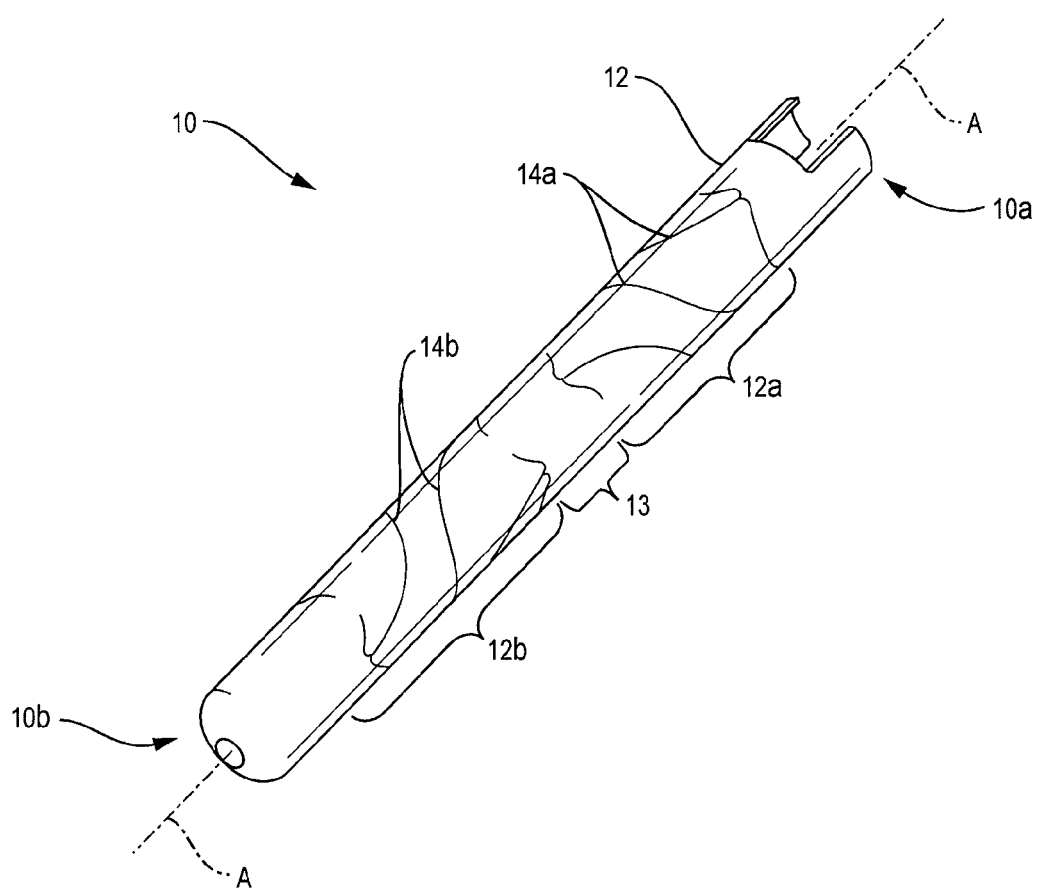
FIG. 1A is a perspective view of one exemplary embodiment of a closure device in an initial, unformed configuration.
Figure 2A:
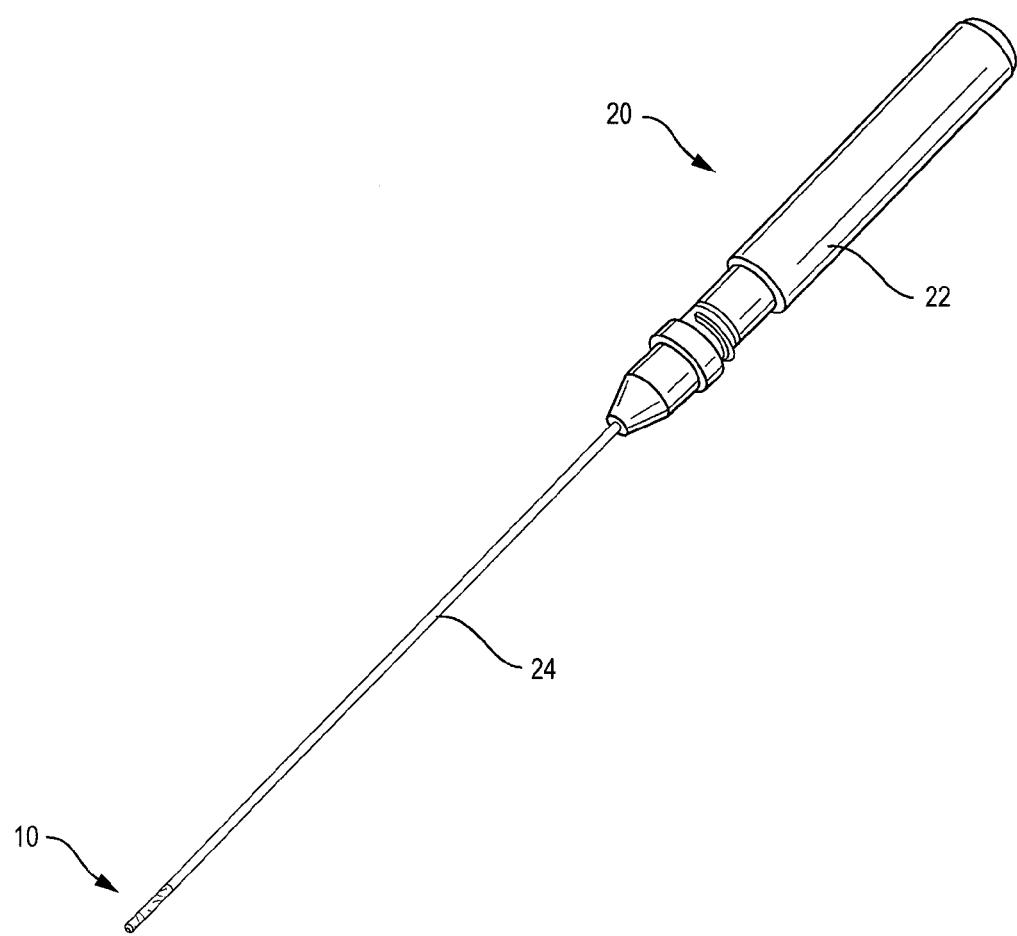
FIG. 2A is a perspective view of one exemplary embodiment of an actuator for deploying a closure device, showing the closure device of FIG. 1A coupled thereto.
Figure 3A:
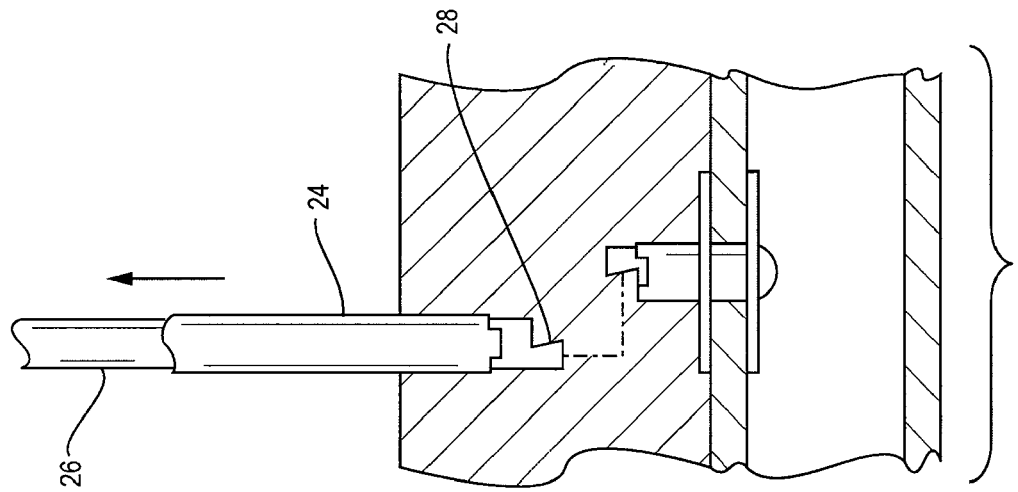
Figure 3B:
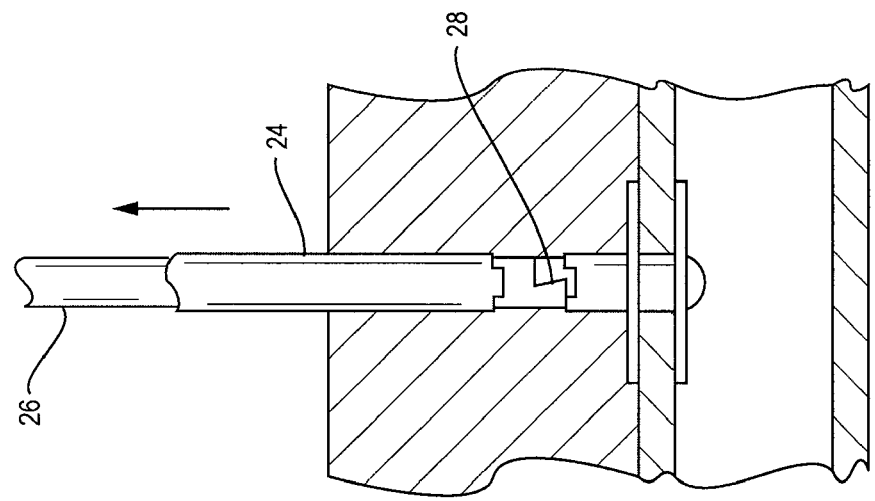
Figure 3C:
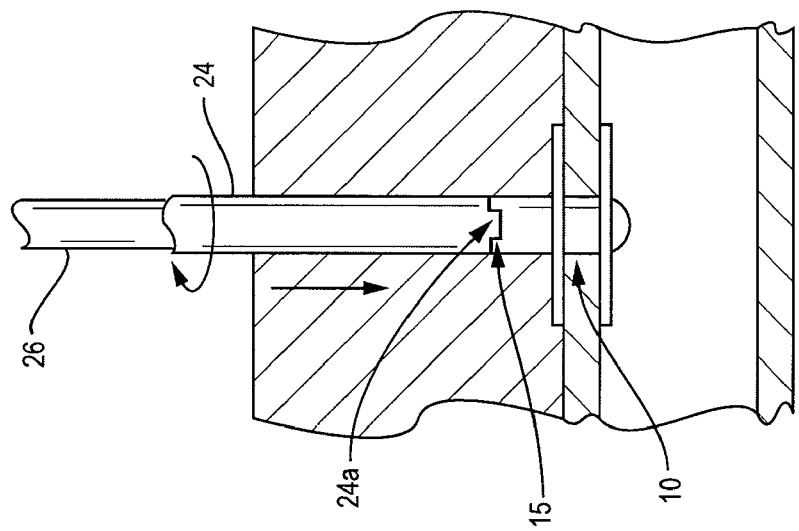
Figure 4A:
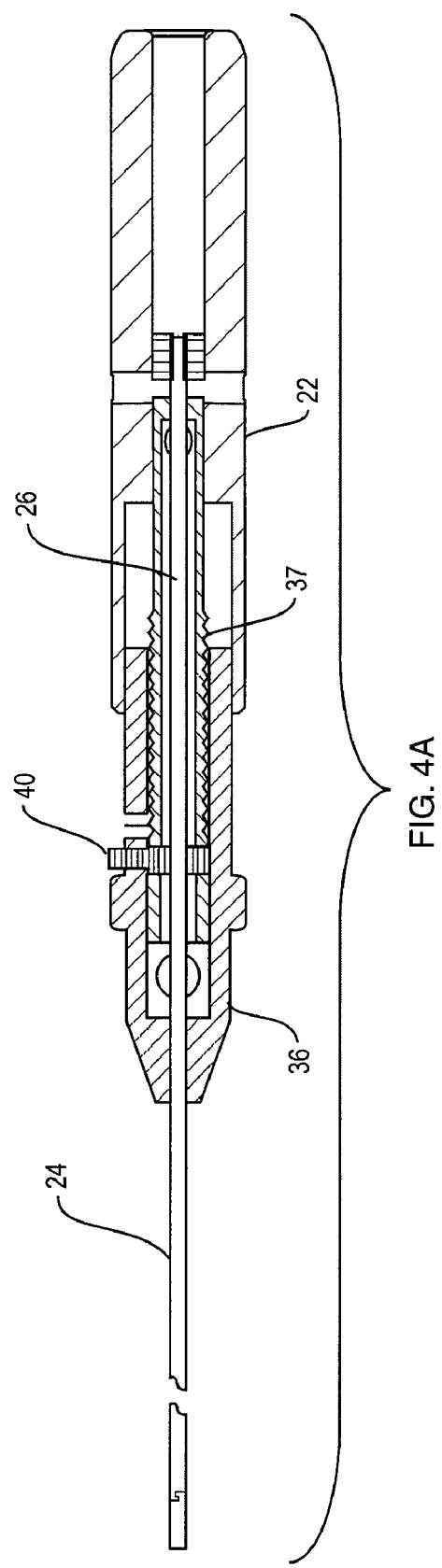
Figure 4D:
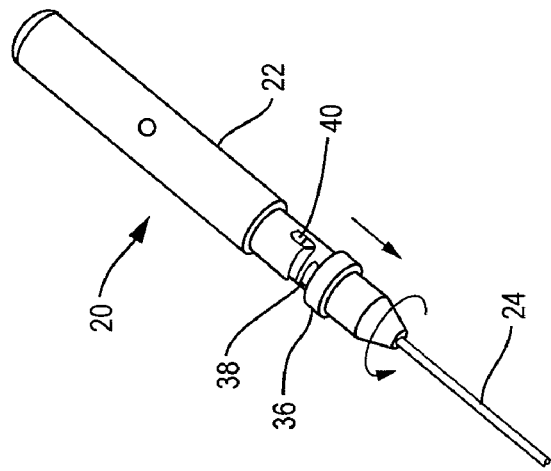
Figure 4C:
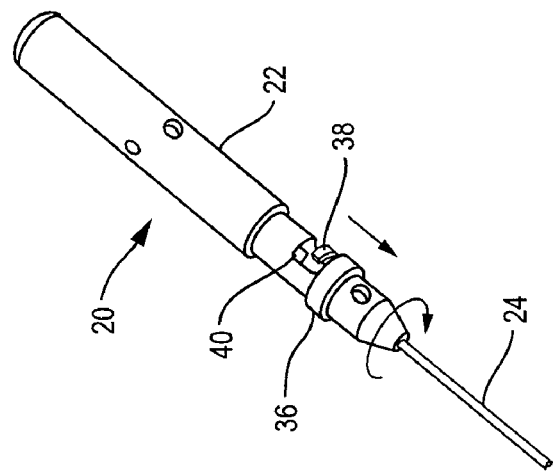
Figure 4B:
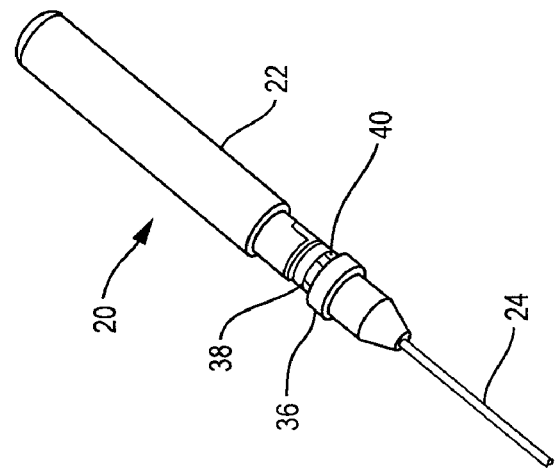
Figure 5:
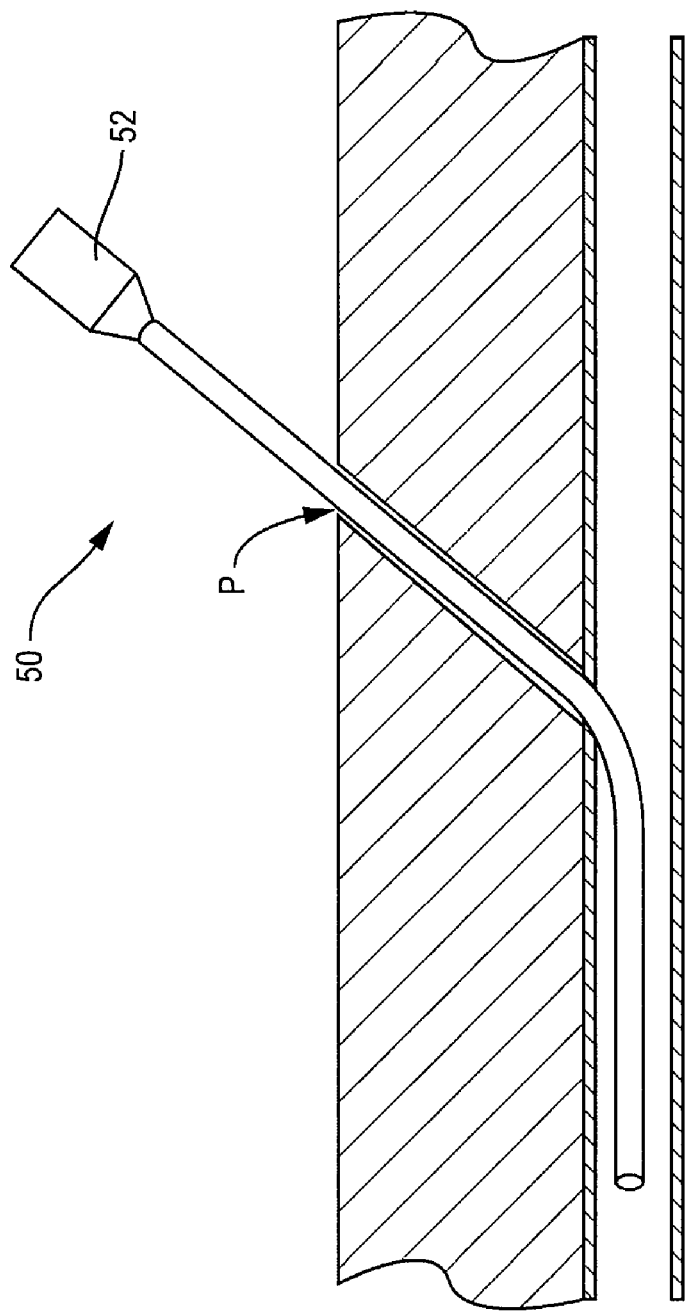
Figure 8B:
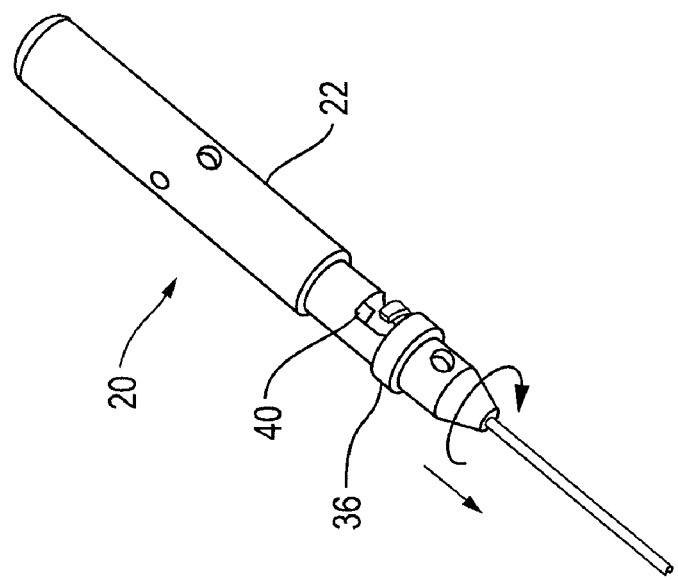
Figure 8A:
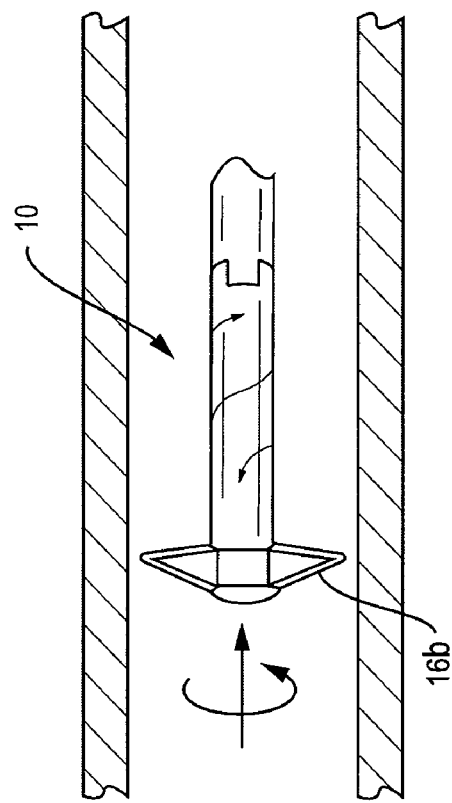
Figure 9:
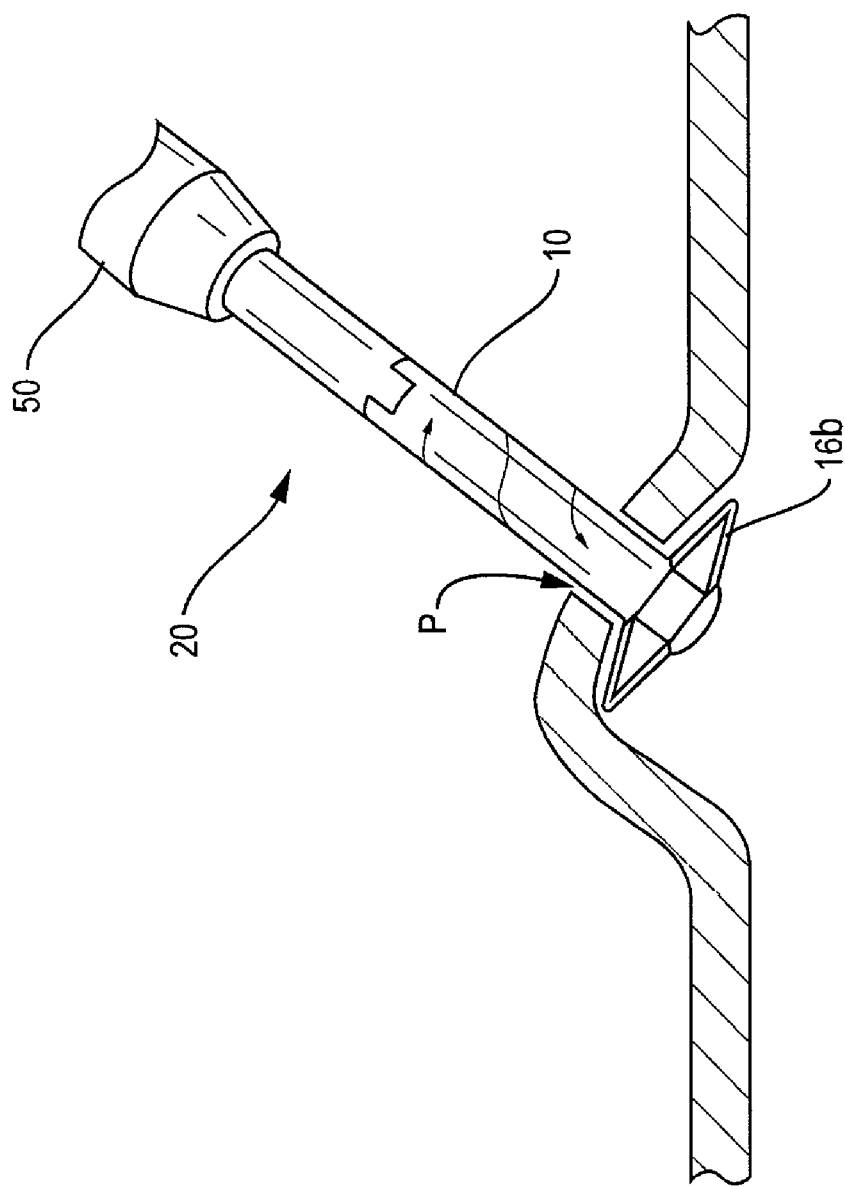
Figure 10B:
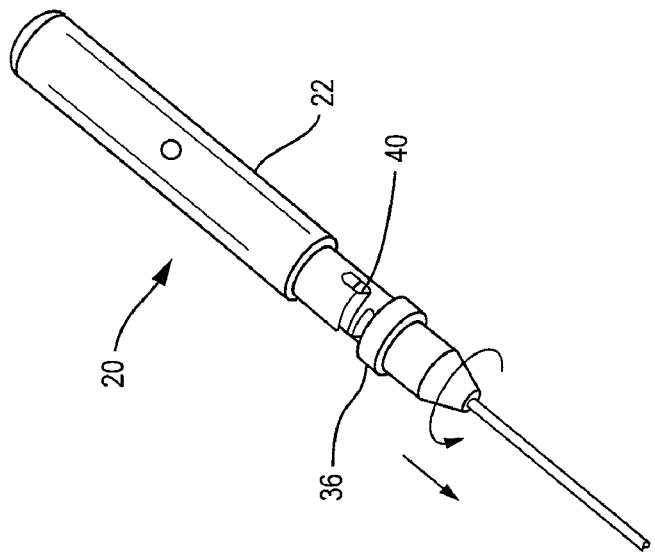
Figure 10A:
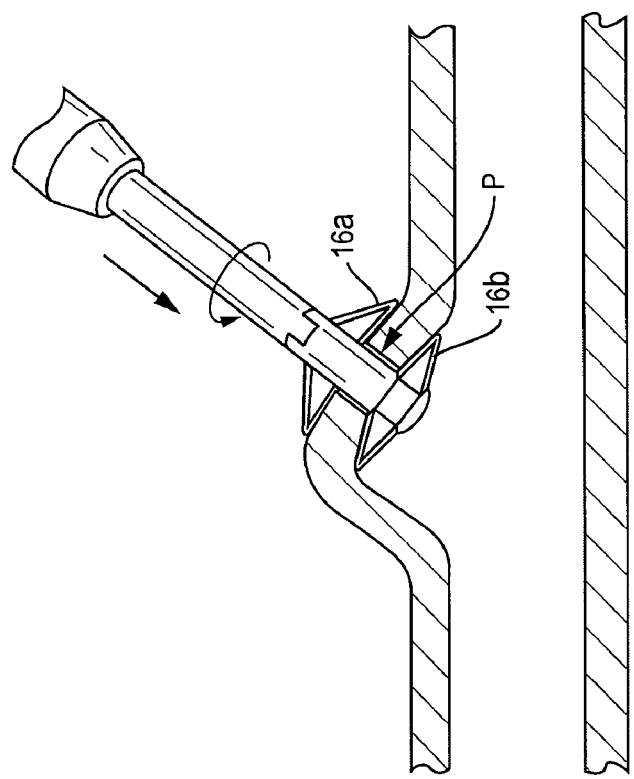

a sequence of steps for deploying the closure device to close a puncture in the wall of an artery;

FIG. 3A is a cross-sectional view of the closure device of FIG. 1A and a portion of the actuator of FIG. 2A, showing the closure device deployed to close a puncture wound in the wall of an artery;

FIG. 3B is a cross-sectional view of the closure device and a portion of the actuator of FIG. 3A following retraction of a former tube of the actuator;

FIG. 3C is a cross-sectional view of the closure device and portion of the actuator of FIG. 4B, following detachment of an inner shaft of the actuator;

FIG. 4A is a cross-sectional view of the handle portion of the actuator of FIG. 2A;

FIG. 4B is a perspective view of a proximal portion of the actuator of FIG. 4A in an initial, starting position;

FIG. 4C is a perspective view of the proximal portion of the actuator shown in FIG. 4B following deployment of the distal wings of a closure device;

FIG. 4D is a perspective view of the proximal portion of the actuator shown in FIG. 4CB following deployment of the proximal wings;

FIG. 5 is a partially cross-sectional view of one embodiment of access sheath disposed a femoral artery;

FIG. 6 is a partially cross-sectional view of the access sheath of FIG. 5 having a closure device and actuator positioned therethrough;

FIG. 7 is a partially cross-sectional view of the access sheath, closure device, and actuator of FIG. 6 with the closure device disposed within the femoral artery;

FIG. 8A is a partially cross-sectional view of the closure device of FIG. 7 following deployment of the distal wings;

FIG. 8B is a perspective view of the actuator of FIG. 7 following deployment of the distal wings;

FIG. 9 is a partially cross-sectional view of the closure device of FIG. 8A retracted to engage the puncture hole;

FIG. 10A is a partially cross-sectional view of the closure device of FIG. 9 with the proximal wings deployed to engage the puncture hole between the proximal and distal wings; and FIG. 10B is a perspective view of the actuator of FIG. 8B following full deployment of the proximal wings of the closure device.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides methods and devices for closing a puncture wound in tissue. In general, the closure device can be in the form of an elongate body that is adapted to be positioned within a puncture, and that includes proximal and distal portions that are configured to radially expand to engage tissue therebetween and thereby close the puncture. FIG. 1A illustrates one exemplary embodiment of such a closure device 10. The device 10 is illustrated in an initial, un-deployed configuration, and as shown the device 10 is in the form of a generally elongate tubular body 12 with a closed or sealed distal end 10b and an open proximal end 10a. The tubular body 12 can be formed from a variety of materials. In an exemplary embodiment, the closure device is formed from a deformable material that undergoes plastic deformation (i.e. deformation with negligible elastic component). Exemplary materials include, by way of non-limiting example, any biocompatible and/or bioabsorbable materials, including, for example, titanium (and titanium alloys), magnesium alloys, stainless steel, polymeric materials (synthetic and/or natural), ceramic, etc. Materials which are not normally radiopaque e.g. Magnesium Alloy, may be enhanced and made x-ray visible with the addition of x-ray visible materials, such as particles of Iron Oxide, stainless steel, titanium, tantalum, platinum or any other suitable equivalents. The elongate tubular body 12 can also be manufactured using various techniques. For example, the body 12 can be formed from a piece of tubing, or it can be formed from sheet stock material. The developed surface of the final tubular shape may be stamped and folded into position. Various joining processes such as welding, soldering, etc. may be used to join any seams.

As indicated above, the device 10 can include one or more portions that expand to engage tissue therebetween and thereby close a puncture. In the embodiment shown in FIG. 1A, the device includes proximal and distal portions 12a, 12b that are configured to expand to engage tissue therebetween. While various techniques can be used to allow the proximal and distal portions 12a, 12b to expand, in an exemplary embodiment the proximal and distal portions 12a, 12b each include a plurality of slits 14a, 14b formed therein and configured to allow portions of the elongate tubular body 12 between the plurality of slits 14a, 14b to radially expand, as will be discussed below. A mid-portion 13 of the tubular body 12, located between the proximal and distal portions 12a, 12b, can be non-expanding and may vary in length. The mid-portion 13 is configured to be positioned within a puncture hole, and thus it can have a length that corresponds to a thickness of the tissue wall. Alternatively, the mid-portion 13 can be configured to expand outward. Openings in the form of holes and slots may be located in the wall of the elongate body 12 at the mid-portion 13.

The slits 14a, 14b in the proximal and distal portions 12a, 12b can extend in any direction and each portion 12a, 12b can include any number of slits. Preferably the slits 14a, 14b are configured such that certain portions of the elongate tubular body 12 between the slits will extend outward away from a central axis A of the tubular body 12 when the body 12 is axially compressed, and preferably rotated as well. As a result, one or more wings will form in each of the proximal and distal portions 12a, 12b to engage tissue therebetween. In an exemplary embodiment, as shown in FIG. 1A, the slits 14a, 14b in the proximal and distal portions 12a, 12b are curved and extend transverse to a central axis A of the elongate tubular body 12 such that they at least partially extend around the elongate tubular body 12. More preferably, the slits 14a in the proximal portion 12a extend in a first direction around a circumference of the elongate tubular body 12 and the slits 14b in the distal portion 12b extend in a second opposite direction around the circumference of the elongate tubular body 12. Such a configuration allows the tubular body 12 to be rotated in a first direction to cause only one of the proximal and distal portions 12a, 12b to radially expand, and then to be rotated in a second direction to cause the other one of the proximal and distal portions 12a, 12b to radially expand. A person skilled in the art will appreciate that the slits 14a, 14b can have a variety of other shapes and sizes, and that they can extend in various directions, such as helical or parallel to the central axis A of the tubular body. The slits 14a, 14b can also include additional curved slits extending from each end of the main slits 14a, 14b to ensure that the end profile of the wings is aligned close to the main body 12 of the closure device 10 following deployment. This can help to ensure a fluid tight seal. These curved end slits can also narrow the width of the tubing section between slits thus encouraging the wings to bend outward at this point.

Figure 1D:
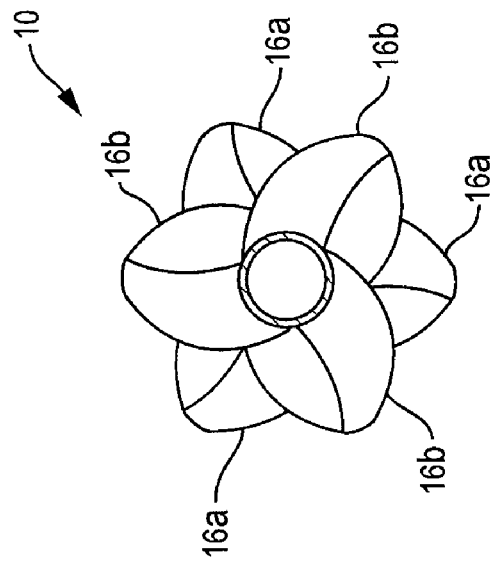
FIG. 1D is an end view of the closure device of FIG. 1A following deployment of the proximal wings.
Figure 1C:
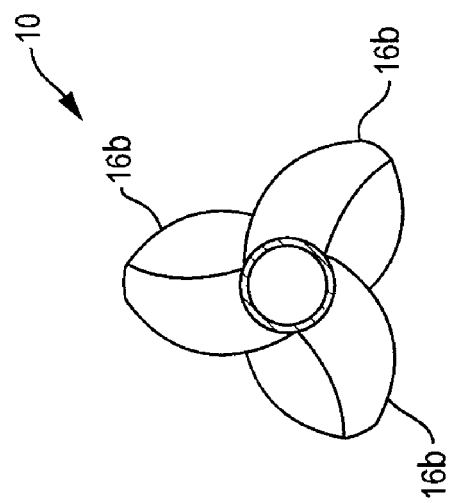
FIG. 1C is an end view of the closure device of FIG. 1A following deployment of the distal wings.
Figure 1B:
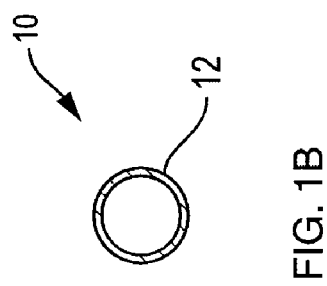
FIG. 1B is a cross-sectional view of the closure device of FIG. 1A prior to deployment.

FIGS. 1B-1C show distal end views of the closure device 10 in its pre-deployed configuration, following partial deployment, and following full deployment, respectively. In the pre-deployed configuration, as shown in FIG. 1B, the elongate tubular body 12 has a diameter that is configured to fit within a puncture hole in a vessel, and that is also preferably configured to fit within an introducer sheath for guiding the device 10 to a puncture site, as will be discussed in more detail below. FIG. 1C illustrates the distal portion 12b radially expanded to form distal wings 16b, and FIG. 1D illustrates the proximal portion 12a radially expanded to form proximal wings 16a. The wings 16a, 16b are formed by the material between the slits 14a, 14b, which is deformed outward as the elongate tubular body 12 is compressed and preferably rotated. In the illustrated embodiment, the slits 14a, 14b are configured such that the proximal and distal portions 12a, 12b each include three wings 16a, 16b, however the proximal and distal portions 12a, 12b can include any number of wings 16a, 16b. The size and shape of the wings 16a, 16b can also vary depending on the location and length of the slits 14a, 14b. In an exemplary embodiment, the size and shape of the wings 16a, 16b is maximized to maximize the contact area between the wings 16a, 16b and the tissue surrounding the puncture hole within which the device 10 is deployed. As shown in FIGS. 1C and 1D, the wings 16a, 16b are substantially ovular and have a generally planar configuration such that the wings 16a, 16b extend substantially parallel to one another. The proximal and distal wings 16a, 16b can also be configured to be offset from one another, as shown in FIG. 1D, to further maximize the contact area around the puncture hole. The proximal and distal wings 16a, 16b are also preferably configured to be positioned a distance apart from one another.

The length of the mid-portion 13 is determinative of the distance between the wings 16a, 16b.

The wings 16a, 16b and/or other portions of the closure device 10 can also optionally include extensions or protrusions which are configured to puncture the engaged tissue. For example, each wing 16a, 16b can include one or more tissue-penetrating protrusions formed thereon. The extensions or protrusions can better facilitate anchoring of the closure device 10 at a puncture site, and they can also be used to facilitate closure of the puncture. During deployment, as will be discussed in more detail below, the extensions or protrusions can puncture the tissue around the puncture wound, and upon rotation of the wings 16a, 16b will twist this tissue in a spiral motion causing it to compress around the puncture and seal the hole.

As indicated above, the wings 16a, 16b on the closure device 10 can be formed by compressing and preferably rotating the closure device 10. While various techniques can be used to deploy and actuate the closure device 10, in one exemplary embodiment the closure device 10 is removably coupled to an actuator that is adapted to apply an axial and rotational force to the elongate tubular body 12 to cause the elongate tubular body 12 to extend outwardly. FIGS. 2A illustrates one exemplary embodiment of an actuator 20 for deploying the closure device 10. In general, the actuator 20 includes a proximal portion in the form of a handle 22, and an elongate shaft extending distally from the handle 22 and having a distal end that is removably coupled to the closure device 10. The elongate shaft preferably includes an outer shaft 24, hereafter referred to as a former 24, that is effective to apply axial and/or rotational forces to the closure device 10, and an inner shaft 26 (shown in FIGS. 2B and 2C) that mates to the closure device 10 and that is effective to hold a portion of the closure device 10 in a fixed position while axial and/or rotational forces are being applied to the closure device 10 to allow the closure device 10 to be deformed, as will be discussed in more detail below. While not shown, the actuator 20 can also include an over sleeve that is attached to the former 24 at its distal end. The sleeve can help prevent separation of the closure device 10 from the actuator 20.

Figure 2B:
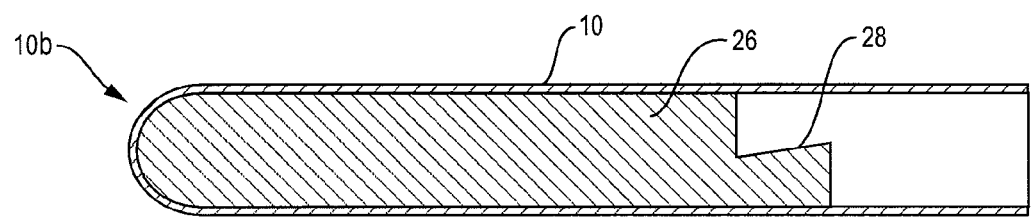
FIG. 2B is a cross-sectional view of the closure device of FIG. 1A and an inner shaft of the actuator of FIG. 2A.

The inner shaft 26 can be coupled to the closure device 10 at a variety of locations and using a variety of techniques. In an exemplary embodiment, the inner shaft 26 is removably coupled to the closure device 10, and more preferably it is frangibly coupled to the closure device 10 to allow at least a portion of the inner shaft 26 to be detached and separated from the closure device 10 after the device is deployed. FIG. 2B illustrates one exemplary embodiment of an inner shaft 26 that is frangibly coupled to the closure device 10 at a frangible portion 28. As shown, the inner shaft 26 extends through the closure device 10 and attaches to the closed distal end 10b of the closure device 10. An adhesive or any other mating technique can be used to attach the distal end of the inner shaft 26 to the distal end 10b of the closure device 10. The frangible portion 28 of the shaft 26 is configured such that it will break when a force is applied thereto. The frangible portion 28 can be formed at any location on the shaft 26, for example, the distal-most end of the shaft 26 can be configured to break away from the distal end 10b of the closure device 10. Alternatively, as shown in FIG. 2B, the frangible portion 28 can be located a distance away from the distal end 10b of the closure device 10, such that a portion of the inner shaft 26 will remain attached to the closure device 10, and the remainder of the inner shaft 26 can be separated from the closure device 10. The frangible portion 28 can be formed using various techniques known in the art. For example, the inner shaft 26 can include a thinned or weakened region. This can be achieved by reducing the amount of material at that region, or by scoring or otherwise removing some of the material used to form the inner shaft 26. In use, the frangible portion 28 can be broken by applying a force, such as a rotational or axial force, to the inner shaft 26. In other embodiments, the inner shaft 26 can be attached to the closure device 10 using a threaded attachment. During use, the inner shaft 26 can be rotated relative to the closure device 10 so as to unscrew the inner shaft 26 from the closure device 10. Once detached, the inner shaft 26 is removed from the patient leaving the closure device 10 in position at the puncture site. A person skilled in the art will appreciate that a variety of mating techniques can be used, including, for example, an interference fit, a mechanical interlock, etc.

Figure 2C:
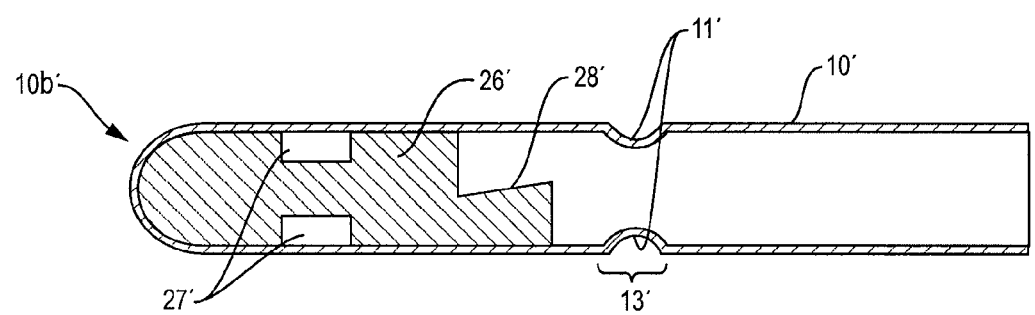
FIG. 2C is a cross-sectional view of another embodiment of the closure device of FIG. 1A and an inner shaft of the actuator of FIG. 2A.

In another embodiment, as shown in FIG. 2C, the inner shaft 26' can include a reduced diameter region 27' formed distal of the frangible portion 28'. The reduced diameter region 27' is preferably configured to be aligned with the mid-portion 13' of the closure device 10' when the closure device 10' is fully deployed. As further shown in FIG. 2C, the closure device 10' can include one or more holes or openings 11' formed in the sidewalls thereof at the mid-portion 13' of the device 10'. In use, the reduced diameter region 27' will be positioned within the puncture wound adjacent to the holes 11'. This will allow blood to enter through the holes 11' to initiate tissue growth, during and following resorption of the closure device 10'.

Figure 2D:
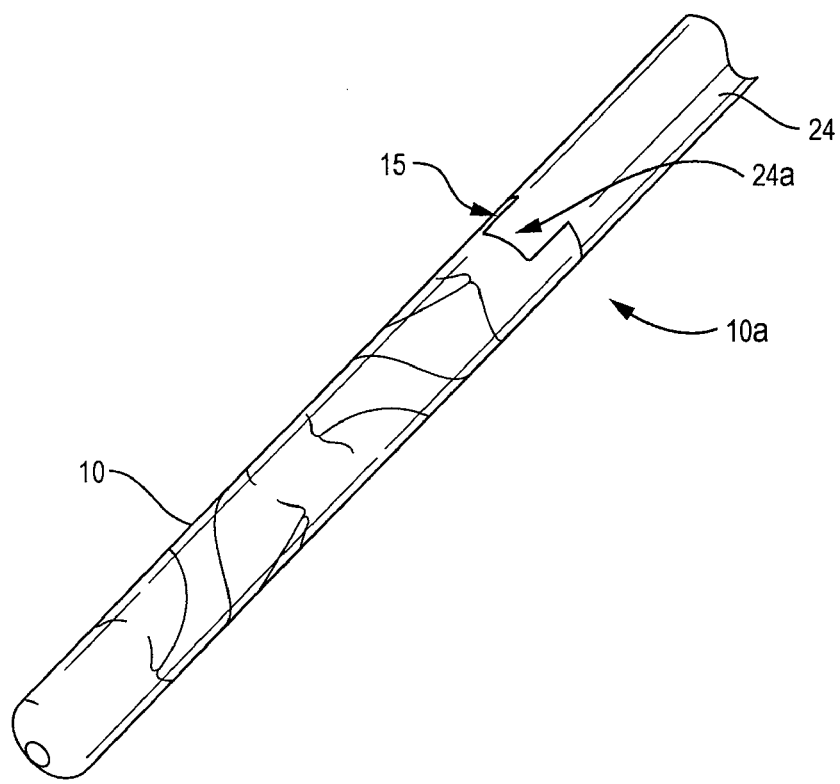
FIG. 2D is a perspective view of a portion of a former tube of the actuator of FIG. 2A coupled to the closure device of FIG. 1A.

As previously indicated, the actuator 20 also includes an outer shaft or former 24 that is disposed around the inner shaft 26 and that is effective to apply axially and/or rotational forces to the closure device 10 to deploy the closure device 10. The former 24 can have a variety of configurations, but it is preferably adapted to couple to a proximal end 10a of the closure device 10. While various techniques can be used to couple to the closure device 10, FIG. 2D illustrates one exemplary technique. As shown, the former 24 includes one or more protrusions 24a that extend into one or more complementary grooves or cut-outs 15 formed in the proximal end of the closure device 10.

Figure 2E:
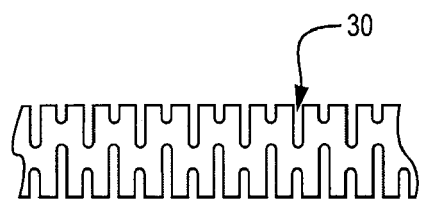
FIG. 2E is a cross-sectional view of another embodiment of a former tube for use with the actuator device of FIG. 2A.
Figure 2F:
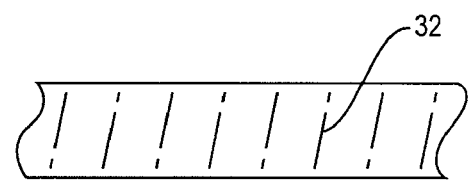
FIG. 2F is a cross-sectional view of yet another embodiment of a former tube for use with the actuator device of FIG. 2A.

The former 24 can also be configured to provide maximum flexibility during clinical use. While the former 24 can merely be formed form a flexible material, in other embodiments the former 24 can include one or more flexible regions formed thereon. FIGS. 2E and 2F show exemplary embodiments of flexible regions. In the embodiment shown in FIG. 2E, the tube includes an interrupted slotted pattern 30. In the embodiment shown in FIG. 2F, the tube includes a spiral slit or interrupted spiral slit 32 cut through the wall of the tube. Such configurations provide flexibility along the length of the former, but can also ensure that an axial and/or rotational force applied to one end of the former will be transmitted along the length of the former to the other end.

FIGS. 3A-3B illustrate a distal portion of the former 24 and inner shaft 26 of the actuator 20 in use with the closure device 10 positioned within a puncture wound and fully deployed to close the puncture. In FIG. 3A, the protrusions 24a on the former 24 are positioned within the corresponding cut-outs 15 formed in the proximal end of the closure device 10, such that the former 24 is mated to the closure device 10. The former 24 can thus be rotated relative to the inner shaft 26, to thereby rotate the proximal and distal portions of the closure device 10 to form proximal and distal wings that engage tissue therebetween, as shown. Following deployment of the closure device 10, the actuator must be disconnected and removed from the patient. FIG. 3B illustrates the former 24 retracted relative to the closure device 10 in order to expose the frangible portion 28 formed on the inner shaft 26. Once exposed, a force can be applied to the inner shaft 26 to break the frangible portion 28, and thereby separate the proximal portion of the shaft 26 from the distal portion of the shaft, which remains coupled to the closure device 10, as shown in FIG. 3C.

In order to effect rotation of the former tube 24 relative to the inner shaft 26, the handle 22 of the actuator 20 can optionally include an actuation mechanism formed thereon. In an exemplary embodiment, as shown in FIGS. 4A-4D, the handle 22 includes an outer collar 36 rotatably disposed therearound and having guide tracks 38 formed therein. The outer collar 36 can be coupled to proximal portion of the former 24 such that rotation of the collar 36 is effective to rotate the former 24. The proximal end of the inner shaft 26 can also include an inner collar 37 that is attached to the inner shaft 26, and that includes pin 40 formed thereon or extending therefrom. The pin 40 extends through and is positioned within the guide tracks 38. Since the position of the pin 40 is fixed due to the inner shaft 26 being fixed, movement of the outer collar 36, and thus the former 24, is governed by the configuration of the guide tracks 38 which can move relative to the fixed pin 40. As a result, the guide tracks 38 can be used to control the axial and rotational forces applied to the closure device 10 coupled to the distal end of the former 24.

As shown in FIGS. 4B-4D, the guide tracks 38 can have a configuration that allows the collar 36 to rotate in a first direction, e.g., counter clockwise, to deploy the distal wings of the closure device. In particular, as the outer collar 36 is rotated counter clockwise, the former tube 24 will rotate in a counter-clockwise direction, thereby rotating the proximal end of the closure device 10 to expand the distal wings of the closure device. As previously discussed, since the slits in the proximal and distal portions preferably extend in opposition directions, rotation of the closure device in a first direction will only deploy the distal wings. Once the outer collar 36 is fully rotated, the guide tracks 38 can allow distal movement of the outer collar 36, while the guide pin 40 remains in a fixed position at all times, thus allowing the outer collar 36 to be advanced distally. As a result, the former tube 24 will apply compressive forces on the closure device, thereby causing the distal wings to collapse into a substantially planar configuration.

The guide tracks 38 can then allow the outer collar 36 to rotate in an opposite direction, e.g., a clockwise direction, to cause the former tube 24 to rotate clockwise. As the former tube 24 rotates clockwise, the proximal wings will expand. Once the outer collar 36 is fully rotated, the guide tracks 38 can allow distal movement of the outer collar 36 therein, thus allowing the outer collar 36 to be advanced distally. As a result, the former tube 24 will apply compressive forces on the closure device, thereby causing the proximal wings to collapse into a substantially planar configuration. The guide tracks 38 can include a track portion that allows the outer collar 36 to be moved proximally, as shown in FIG. 4C, to allow the former 24 to be retracted relative to the closure device 10, thereby exposing the frangible portion on the inner shaft.

A person skilled in the art will appreciate that the guide tracks 38 can have a variety of other configurations. For example, rather than allowing rotation, and then distal movement, the guide tracks 38 can extend at an angle around the handle 22 to allow rotational and compressive forces to be simultaneously applied to the closure device. A person skill in the art will appreciate that a variety of other techniques can be used to actuate the former 24 to deploy the closure device.

The present invention also provides exemplary methods for closing a puncture wound. While various devices can be used to effect the method, FIGS. 5-9 illustrate an exemplary method for closing a puncture wound using the closure device 10 of FIG. 1A and the actuator 20 of FIG. 2A. During therapeutic or diagnostic procedures, an access sheath is commonly placed within the vessel, e.g., the femoral artery, to facilitate delivery of catheters into the vascular system. The access sheath 50, as illustrated in FIG. 5, typically includes a hub 52 at its proximal end incorporating a valve to prevent blood leakage. However, the valve can be configured to facilitate entry of components into the sheath 50 and onward into the puncture wound or vasculature. Prior to delivery of the closure device, the access sheath 50 is advanced fully into the puncture wound P until the hub 52 is in contact with the patient's skin. The former 24 of the actuator 20 is then advanced through the access sheath hub 52 and onward through the sheath 50, as shown in FIG. 6. In an exemplary embodiment, the former tube 24 can include a marker formed thereon that can be aligned with the proximal most end of the hub 52 on the access sheath 50 so as to retain the closure device 10 within the access sheath 50 and thereby prevent trauma to the wall of the vessel. While holding the actuator in position, the access sheath 50 can be pulled back along the former 24 until it contacts the handle 22 on the actuator 20, as shown in FIG. 7. The closure device 10 is now exposed within the lumen of the vessel and is ready for deployment.

Alternatively, a side hole may be positioned in the wall of the closure device 10 or in the wall at the distal end of the former tube 24. This hole can open into a tubular channel leading to the actuator handle 22. As the actuator 20 is advanced through the sheath 50, the side hole is not in contact with blood flow. Once the closure device 10 and/or the distal end of the former 24 exits the sheath 50 into the femoral artery, blood will enter the side hole and advance through the channel to exit at the actuator handle 22. This will signal to the user that the closure device 10 is now in the blood lumen, and no further advancing is required and the device 10 is ready for deployment.

In other embodiments, the device 10 may be delivered to the artery lumen over a guidewire. The proximal end of the guidewire, which extends from the patient, can be inserted into an opening at the distal tip of the closure device 10. It can extend through the shaft and handle 22 of the actuator 20, or in other embodiments it can exit through a side hole located either in the closure device 10 or at the distal end of the former tube 24.

Once the closure device 10 is positioned to be deployed, the outer collar 36 on the handle 22 of the actuator 20 can be rotated in a first, e.g., counter-clockwise as shown in FIG. 8B, to cause the distal portion of the closure device 10 to expand away from the central axis. A compressive force can simultaneously or subsequently be applied to the closure device 10 to cause the expanded portions of the closure device 10 to collapse, and thereby form distal wings 16*b*, as shown in FIG. 8A.

Following deployment of the distal wings 16*b*, the actuator 20 and access sheath 50 can be retracted from the patient until tension is felt indicating the correct position of the distal wings 16*b* at the internal surface of the puncture site, as shown in FIG. 9. The proximal wings can now be deployed in order to complete the closure of the puncture hole P. This is achieved by rotating the actuator outer collar 36 in an opposite direction, e.g., a clockwise direction, as shown in FIG. 10B. This in turn causes the former tube 24 to rotate the proximal end of the closure device 10 in a clockwise direction causing the proximal portion of the closure device 10 to expand outward. The former tube 24 can be simultaneously or subsequently advanced distally causing the expanded portions of the closure device 10 to collapse and form proximal wings 16a, as shown in FIG. 10A. As a result, the proximal and distal wings 16a, 16b engage the tissue surrounding the puncture P therebetween. The closure device 10 is now completely deployed and the puncture hole P sealed. The actuator 20 can be removed as previously discussed.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A puncture closure device, comprising:
an elongate tubular body disposable through a puncture in tissue and having proximal and distal portions, the proximal portion having a plurality of proximal slits formed therein extending in a first direction around a circumference of the elongate tubular body, the proximal slits being configured to allow portions of the elongate tubular body surrounding the plurality of proximal slits to expand to form proximal wings upon rotation of the elongate tubular body in a first direction, and the distal portion having a plurality of distal slits formed therein extending in a second opposite direction around the circumference of the elongate tubular body, the distal slits being configured to allow portions of the elongate tubular body surrounding the plurality of distal slits to expand to form distal wings upon rotation of the elongate tubular body in a second direction opposite to the first direction, whereby the proximal and distal wings are adapted to engage tissue therebetween, the proximal and distal slits having terminal ends with additional slits extending therefrom in opposite directions.

2. The puncture closure device of claim 1, wherein the proximal and distal portions are adapted to be moved toward one another as they expand upon rotation.

3. The puncture closure device of claim 1, further comprising an elongate shaft extending through and attached to a distal end of the elongate tubular body.

4. The puncture closure device of claim 3, wherein the elongate shaft includes a frangible portion configured to allow at least a proximal portion of the elongate shaft to be broken away from a distal portion of the elongate shaft.

5. The puncture closure device of claim 1, further comprising an actuator coupled to the elongate tubular body and adapted to rotate at least a portion of the elongate tubular body.

6. The puncture closure device of claim 5, wherein the actuator is removably coupled to a proximal end of the elongate tubular body.

7. The puncture closure device of claim 1, wherein the proximal wings extend in a plane that is substantially parallel to a plane in which the distal wings extend.

8. The puncture closure device of claim 1, wherein the proximal and distal wings are spaced a distance apart from one another.

9. The puncture closure device of claim 1, wherein the elongate tubular body is formed from a deformable material.

10. The puncture closure device of claim 1, wherein the elongate tubular body is formed from a resorbable material.

11. A system for closing a puncture in tissue, comprising:
an elongate tubular body having proximal and distal portions with a plurality of slits formed therein, wherein the plurality of slits in the proximal portion extend in a first direction around a circumference of the elongate tubular body and the plurality of slits in the distal portion extend in a second opposite direction around the circumference of the elongate tubular body, the elongate tubular body being adapted to extend outwardly between each of the plurality of slits formed in the proximal and distal portions such that the proximal and distal portions are adapted to engage tissue therebetween, the plurality of slits having terminal ends with additional slits extending therefrom in opposite directions; and
an actuator removably coupled to the elongate tubular body and adapted to apply an axial and rotational force to the elongate tubular body to cause the elongate tubular body to rotate and extend outwardly.

12. The system of claim 11, further comprising a mid-portion formed between the proximal and distal portions and adapted to be positioned within a puncture hole formed in tissue engaged between the proximal and distal portions.

13. The system of claim 11, wherein the proximal portion is adapted to extend outwardly when rotated in a first direction, and the distal portion is adapted to extend outwardly when rotated in a second opposite direction.

14. The system of claim 11, wherein the actuator includes an elongate shaft extending therethrough and attached to a distal end of the elongate tubular body.

15. The system of claim 14, wherein the elongate shaft includes a frangible portion configured to allow at least a proximal portion of the elongate shaft to be broken away from a distal portion of the elongate shaft.

16. The system of claim 15, wherein the actuator includes an outer shaft removably coupled to a proximal end of the elongate tubular body, the outer shaft being rotatable relative to the elongate shaft.

17. The system of claim 16, wherein the outer shaft includes a protrusion formed thereon and adapted to extend into a corresponding groove formed on the proximal end of the elongate tubular body for removably coupling the outer shaft to the elongate tubular body.

18. The system of claim 11, wherein the proximal and distal portions form proximal and distal wings when the proximal and distal portions are extended outwardly.

19. The system of claim 18, wherein the proximal wings extend in a plane that is substantially parallel to a plane in which the distal wings extend.

20. The system of claim 18, wherein the proximal and distal wings are spaced a distance apart from one another.

21. The system of claim 11, wherein the elongate tubular body is formed from a deformable material.

22. The system of claim 11, wherein the elongate tubular body is formed from a resorbable material.

23. The system of claim 22, wherein at least a portion of the actuator coupled to the elongate tubular body is formed from a resorbable material.

24. The puncture closure device of claim 1, wherein the proximal and distal wings are substantially ovular and have a generally planar configuration in an expanded configuration.

25. The puncture closure device of claim 1, wherein a width of at least one of the proximal and distal wings is greater than a distance between two adjacent slits of the plurality of slits.

26. The puncture closure device of claim 1, wherein the plurality of slits are curved.

27. The system of claim 11, wherein the actuator is adapted to apply a rotational force is applied to the elongate tubular body to cause the elongate tubular body to extend outward prior to applying an axially compressive force to the elongate tubular body.

28. The system of claim 18, wherein the proximal and distal wings are substantially ovular and have a generally planar configuration in an expanded configuration.

29. The system of claim 18, wherein a width of at least one of the proximal and distal wings is greater than a distance between two adjacent slits of the plurality of slits.

30. The system of claim 18, wherein the plurality of slits are curved.

31. A puncture closure device, comprising:
an elongate tubular body disposable through a puncture in tissue and having proximal and distal portions, the proximal and distal portions each having a plurality of slits formed therein and extending around a circumference of the elongate tubular body, the slits being configured to allow portions of the elongate tubular body surrounding the plurality of slits to expand to form proximal and distal wings upon rotation of the elongate tubular body, the plurality of slits having terminal ends with additional slits extending therefrom in opposite directions, and wherein only the proximal portion can expand to form proximal wings upon rotation of the proximal and distal portions of the elongate tubular body relative to one another in a first direction, and only the distal portion can expand to form distal wings upon rotation of the proximal and distal portions of the elongate tubular body relative to one another in a second opposite direction, and whereby the proximal and distal wings are adapted to engage tissue therebetween.

32. The puncture closure device of claim 31, where the proximal and distal portions are adapted to expand upon rotation of the elongate tubular body prior to applying an axially compressive force to the elongate tubular body.

33. The puncture closure device of claim 31, wherein a width of at least one of the proximal and distal wings is greater than a distance between two adjacent slits of the plurality of slits.

34. The puncture closure device of claim 31, wherein the plurality of slits are curved.

35. The puncture closure device of claim 31, further comprising an elongate shaft extending through and attached to a distal end of the elongate tubular body, the elongate shaft including a frangible portion configured to allow at least a proximal portion of the elongate shaft to be broken away from a distal portion of the elongate shaft.

36. The puncture closure device of claim 31, further comprising an actuator coupled to the elongate tubular body and adapted to apply a rotation force to the elongate tubular body.

37. The puncture closure device of claim 31, wherein the proximal and distal wings are substantially ovular and have a generally planar configuration in an expanded configuration.

38. The puncture closure device of claim 1, wherein the proximal wings are formed upon rotation of the elongate tubular body in the first direction prior to compressing the elongate tubular body and the distal wings are formed upon rotation of the elongate tubular body in the second direction prior to compressing the elongate tubular body.

39. The puncture closure device of claim 1, wherein the distal portion is adapted to expand upon application of a first rotational force to the elongate tubular body in a first direction and the proximal portion is adapted to expand upon application of a second opposite rotational force to the elongate tubular body in a second opposite direction, wherein the first and second rotational forces are applied to the proximal portion.

40. The puncture closure device of claim 39, wherein the second rotational force is applied after the first rotational force.

* * * * *

UNITED STATES PATENT AND TRADEMARK OFFICE
CERTIFICATE OF CORRECTION

PATENT NO. : 7,625,392 B2 Page 1 of 1
APPLICATION NO. : 11/307372
DATED : December 1, 2009
INVENTOR(S) : Coleman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 667 days.

Signed and Sealed this

Twenty-first Day of December, 2010

David J. Kappos
*Director of the United States Patent and Trademark Office*